US006754375B1

(12) United States Patent
Noblett et al.

(10) Patent No.: US 6,754,375 B1
(45) Date of Patent: Jun. 22, 2004

(54) METHOD AND SYSTEM FOR INTERACTIVELY DEVELOPING AT LEAST ONE GRID PATTERN AND COMPUTER-READABLE STORAGE MEDIUM HAVING A PROGRAM FOR EXECUTING THE METHOD

(75) Inventors: David A. Noblett, Oak Park, CA (US); Todd J. Stephan, Santa Clarita, CA (US); Jun Yang, Santa Monica, CA (US)

(73) Assignee: Packard Bioscience Company, Meriden, CT (US)

( * ) Notice: Subject to any disclaimer, the term of this patent is extended or adjusted under 35 U.S.C. 154(b) by 0 days.

(21) Appl. No.: 09/356,168

(22) Filed: Jul. 16, 1999

(51) Int. Cl.[7] ................................................. G06K 9/00
(52) U.S. Cl. ....................... 382/129; 345/619; 382/133; 382/173; 382/291; 422/62; 435/6; 436/43
(58) Field of Search ............. 435/6, 7.21; 382/128–134; 345/433, 619, 629; 422/62; 436/43

(56) References Cited

U.S. PATENT DOCUMENTS

| | | | | |
|---|---|---|---|---|
| 5,591,981 | A | * | 1/1997 | Heffelfinger et al. .... 250/458.1 |
| 5,680,514 | A | | 10/1997 | Shams |
| 5,745,660 | A | * | 4/1998 | Kolpatzik et al. ......... 358/3.19 |
| 5,759,781 | A | * | 6/1998 | Ward et al. ..................... 435/6 |
| 5,814,454 | A | * | 9/1998 | Ju .................................. 435/6 |
| 6,007,994 | A | * | 12/1999 | Ward et al. ..................... 435/6 |
| 6,127,129 | A | * | 10/2000 | Corn et al. ..................... 435/6 |
| 6,165,734 | A | * | 12/2000 | Garini et al. ............... 435/7.21 |
| 6,203,977 | B1 | * | 3/2001 | Ward et al. ..................... 435/6 |
| 6,262,746 | B1 | * | 7/2001 | Collins ........................ 345/433 |
| 6,349,144 | B1 | * | 2/2002 | Shams ......................... 382/129 |
| 6,362,832 | B1 | * | 3/2002 | Stephan et al. ............. 345/629 |

OTHER PUBLICATIONS

Biodiscovery, Inc.: User's Manual, ImaGene Version 2.0, Online, 1998, XP–002161839.
Imaging Research Inc., Chapter 3: Array Vision Tutorial, ARV Version 4.0, Online, Feb. 2, 1999, XP–002161840.
Eisen, Michael, ScanAlyze User Manual, Online, Jul. 14, 1999, XP–002161841.
Scanalytics, Inc., MicroArray Suite Supplement, User's Guide, Online, 1989–1999, XP–002161842.
Lehrach, Hans, et al., Robotics, Computing, and Biology An Interdisciplinary Approach to the Analysis of Complex Genomes, Interdisciplinary Science Reviews, vol. 22, No. 1, 1997, XP–000863340.
General Scanning Inc., View Engineering Division, Model 880 Version 4.0 Software System Administrator's Manual, 1996.

* cited by examiner

*Primary Examiner*—Bhavesh M. Mehta
*Assistant Examiner*—Gregory Desire
(74) *Attorney, Agent, or Firm*—Brooks Kushman P.C.

(57) ABSTRACT

Method and system are disclosed for interactively developing at least one grid pattern, such as a microarray pattern, as well as an array set of such patterns, and a computer-readable storage medium having a program for executing the method given only a few user inputs through the use of a pointing device such as a mouse or trackball on a personal computer or workstation. Each array in the set typically has an identical number of rows and columns of points.

54 Claims, 6 Drawing Sheets

METHOD AND SYSTEM FOR INTERACTIVELY DEVELOPING AT LEAST ONE GRID PATTERN AND COMPUTER-READABLE STORAGE MEDIUM HAVING A PROGRAM FOR EXECUTING THE METHOD

TECHNICAL FIELD

This invention relates to methods and systems for interactively developing at least one grid pattern such as a microarray pattern, as well as an array set of such patterns, and a computer-readable storage medium having a program for executing the methods.

BACKGROUND ART

An array pattern can be used to establish the expected locations of spots containing fluorescently labeled DNA samples on a suitable carrier such as a microscope slide or membrane. These are commonly known as microarrays or bio-chips. The locations are typically used in subsequent quantitative analysis using software and image processing algorithms.

An example of a process that is arranged in a grid pattern is the microarray. As previously mentioned, microarrays are created with fluorescently labeled DNA samples in a grid pattern consisting of rows 22 and columns 20 typically spread across a 1 by 3 inch glass microscope slide 24 as illustrated in FIG. 1. The rows 22 extend along the smaller dimension of the slide 24 and the columns 20 extend along the larger dimension of the rectangular slide 24. Each spot 26 in the grid pattern (or array) 28 represents a separate DNA probe and constitutes a separate experiment. A plurality of such grid pattern comprises an array set 30. Reference or "target" DNA (or RNA) is spotted onto the glass slide 24 and chemically bonded to the surface. Fluorescently labeled "probe" DNA (or RNA) is introduced and allowed to hybridize with the target DNA. Excess probe DNA that does not bind is removed from the surface of the slide in a subsequent washing process.

The purpose of the experiment is to measure the binding affinity between the probe and target DNA to determine the likeness of their molecular structures: complementary molecules have a much greater probability of binding than unrelated molecules. The probe DNA is labeled with fluorescent labels that emit light when excited by an external light source of the proper wavelength. The brightness of each sample on the slide 24 is a function of the fluor density in that sample. The fluor density is a function of the binding affinity or likeness of the probe molecule to the target molecule. Therefore, the brightness of each sample can be mapped to the degree of similarity between the probe DNA and the target DNA in that sample. On a typical microarray, up to tens of thousands of experiments can be performed simultaneously on the probe DNA, allowing for a detailed characterization of complex molecules.

Scanning laser fluorescence microscopes or microarray readers can be used to acquire digital images of the emitted light from a microarray as illustrated in FIG. 2. The digital images are comprised of several thousand to hundreds of millions of pixels that typically range in size from 5 to 50 microns. Each pixel in the image is typically represented by a 16 bit integer, allowing for 65,535 different grayscale values. The microarray reader sequentially acquires the pixels from the scanned microarray and writes them into an image file and stored on a computer hard drive.

As illustrated in FIG. 2, a confocal laser microarray scanner or microarray reader is commonly used to scan the microarray slide 24 to produce one image for each dye used by sequentially scanning the microarray with a laser of a proper wavelength for the particular dye. Each dye has a known excitation spectra as illustrated in FIG. 3 and a known emission spectra as illustrated in FIG. 4. The scanner includes a beam splitter 32 which reflects a laser beam 34 towards an objective lens 36 which, in turn, focuses the beam at the surface of slide 24 to cause fluorescence spherical emission. A portion of the emission travels back through the lens 36 and the beam splitter 32. After traveling through the beam splitter 32, the fluorescence beam is reflected by a mirror 38, travels through an emission filter 40, a focusing detector lens 42 and a central pinhole 44. After traveling through the central pinhole 44, the fluorescence beam is detected by a detector, all in a conventional fashion.

Analysis and Quantitation of the Microarray

Analysis of the fluor density at each spot location requires software that utilize image processing algorithms to locate all the spots and measure the brightness of the pixels in each spot. Typical image processing algorithms utilize one or more methods of thresholding the image to differentiate the background from a spot. Fixed and dynamic thresholding algorithms can be used depending upon the amount of variability of the background brightness across the image. Local area thresholding can also be used to minimize the negative affect of a variable background brightness.

Once a valid threshold is obtained, a temporary image of a lower number of grayscales, typically a binary image with two different grayscales, is created that clearly shows the background separated from the spots. The next step is typically to run a deformable grid algorithm to quantify the X and Y locations of each spot. The deformable grid algorithm is required to account for microarray manufacturing variations that commonly occur causing the spot positions to vary on an irregular basis. In order to measure the true brightness levels at each spot, the true spot position must be measured in real time since it can vary from array to array and from microarray to microarray.

Once the location of each spot is determined, additional image processing algorithms calculate the spot brightness of each spot. This is done with the original full resolution image. Typically, a sophisticated dynamic local area threshold technique is calculated using pixels within the local area 38 which belong to the background 40 and which belong to the spot 26 as illustrated in FIG. 3. Only the pixels that represent the spot 26 are used to calculate the brightness value for that spot 26. The final brightness value is typically calculated as the mean, mode, or sum of the pixels that represent the spot 26. The brightness value of the background 40 is also important to researchers, and is calculated in similar manner by the mean, mode, or sum of the pixels that represent the local background 40.

The location and analysis of spots and background process continues for each image obtained from the microarray sample by the microarray reader. The number can vary from one to four or more images per microarray and depends upon the number of differently labeled probe DNA samples used in the creation of the microarray.

The Need for a Regular Grid Pattern and How to Create One.

In order for a researcher to calculate the brightness of each spot and local background, also known as to "quantitate" the microarray, of a large microarray pattern, he/she must create a map or pattern of the microarray spot locations. To perform quantitation on a small number of spots, typically less than 100, a user can manually locate the spot. Manual location of spot patterns with more than 100 spots become cumbersome while larger arrays are impossible to quantitate in this manner. Also, with the progression of the microarray inspection towards automation, efficient and accurate methods to create the array patterns and quantitate the spots will be required. The microarray map is a template that is used by the software to efficiently search for the true locations of each spot in the pattern.

To fully describe a regular grid pattern, several parameters are required—the number of rows of spots, the number of columns of spots, the distance between each row, the distance between each column, and the average diameter of each spot. The most straightforward way of creating a regular grid pattern would be to manually enter appropriate values for each of the parameters above. This method, however, requires a-priori knowledge of the complete pattern of the array. This information is difficult to obtain because of the variation in microarray fabrication methods, typically either by hand and by automatic array spotting equipment, and the wide range of variability in each method.

The regular grid pattern is extended in common practice in the fabrication of microarrays to produce several copies of the same basic grid pattern across the microarray (manually though). These patterns are denoted as the array set 30 in FIG. 1. The additional parameters required to specify the array set are the number of arrays in each row, the number of arrays in each column, the distance between the upper left spot in each array along a row, and the distance between the upper left spot in each array along a column.

A company named BioDiscovery has a commercially available quantitation software package named ImaGene™. This software package requires the researcher to manually type in the number of rows and columns of spots for the array, and point to and click on the four corner spots 42 of the array 44, to be able to calculate the row and column spacing values as shown in FIG. 4. Additionally, to create array sets, the software requires the researcher to enter the number of arrays in the set 46 along both the row and column direction and point to and click on the upper left spot 48 in each of the four corner arrays. The array spacing along the row and column are calculated by the software.

U.S. Pat. No. 5,680,514 discloses a multiple elastic feature net and a method for target deghosting and tracking.

SUMMARY OF THE INVENTION

An object of the present invention is to provide a method and system for interactively developing at least one grid pattern, such as a microarray pattern, as well as an array set of such patterns, and a computer-readable storage medium having a program for executing the method wherein a user need not know the number of rows or columns before creating the array pattern.

Another object of the present invention is to provide a method and system for interactively developing at least one grid pattern, such as a microarray pattern, as well as an array set of such patterns, and a computer-readable storage medium having a program for executing the method wherein a user can create an accurate array pattern without any knowledge of the physical dimensions of the microarray pattern.

Yet another object of the present invention is to provide a method and system for interactively developing at least one grid pattern, such as a microarray pattern, as well as an array set of such patterns, and a computer-readable storage medium having a program for executing the method wherein the software automatically records the required dimensions without manual entry by the user.

In carrying out the above objects and other objects of the present invention, a method for interactively developing at least one grid pattern from at least one digital image of rows and columns of spots is provided. The method includes displaying the rows and columns of spots including a corner spot located in one of the rows and columns. The method also includes receiving a first set of commands from a user to select an approximate location of the corner spot to obtain pattern origin data. The method then includes processing the at least one digital image and the pattern origin data to obtain the at least one grid pattern. The at least one grid pattern includes rows and columns of grid elements and wherein the step of processing includes the step of calculating the number of rows and columns of grid elements, average spacing between adjacent rows and average spacing between adjacent columns of grid elements.

The method may also include receiving a second set of commands from a user to select at least one edge of one of the spots to obtain spot dimension data. The spot dimension data is then processed with the pattern origin data and the at least one digital image to obtain the at least one grid pattern.

The method may include receiving a third set of commands from a user to select at least one row spot in the same row as the corner spot to obtain row data. The at least one row spot includes a spot furthest away from the corner spot. The row data is then processed with the pattern origin data and the at least one digital image to obtain the at least one grid pattern.

The method may further include receiving a fourth set of commands from a user to select at least one spot in the same column as the corner spot to obtain column data. The at least one column spot includes a spot furthest away from the corner spot. The column data is then processed with the pattern origin data and the at least one digital image to obtain the at least one grid pattern.

Preferably the step of receiving the second set of commands from the user selects two opposite edges of the one of the spots and wherein the spot dimension data is spot diameter data.

Also, preferably, the step of receiving the third set of commands selects two row spots in the same row as the corner spot to obtain the row data.

The step of receiving the fourth set of commands selects two column spots in the same column as the corner spot to obtain the column data.

The at least one grid pattern may be a microarray pattern.

The method may be extended to interactively develop a regular pattern of grid patterns including the at least one grid pattern from the at least one digital image. The regular pattern of grid patterns defines an array set. The rows and columns of spots define rows and columns of arrays. The method further includes receiving a fifth set of commands from a user to select at least one row corner spot in the row of arrays corresponding to the corner spot of the at least one grid pattern to obtain row array data. The at least one row corner spot is in an array furthest from the at least one grid pattern in the same row of arrays as the at least one grid pattern. The method further includes receiving a sixth set of commands from a user to select at least one column corner spot in the column of arrays corresponding to the corner spot of the at least one grid pattern to obtain column array data. The at least one column corner spot is in an array furthest from the at least one grid pattern in the same column of arrays. The step of processing also processes the row array data and the column array data with the spot dimension data, the pattern origin data and the row and column data to obtain the regular pattern of grid patterns.

Each of the grid patterns may be a microarray pattern.

Preferably, the step of receiving the fifth set of commands selects two row corner spots in the same row of arrays as the at least one grid pattern to obtain the row array data.

The step of receiving the sixth set of commands preferably selects two column corner spots in the same column of arrays as the at least one grid pattern to obtain the column array data.

The method may further include displaying a value representing distance between columns or rows of spots.

Preferably, the step of processing includes the step of processing the spot dimension data and the pattern origin data to obtain a bounded area of image data which encompasses either the row or the column of spots including the corner spot. The step of processing further includes the step of performing a profile projection of the image data in the bounded area to obtain profile projection data. The step of processing also includes the step of calculating a spot model projection based on the spot dimension data. The step of processing then includes the steps of utilizing the spot model projection as a correlation model and comparing the correlation model with sections corresponding to each spot along the profile projection in the bounded area. Still further, the step of processing includes the step of calculating a correlation coefficient between the correlation model and each similar feature within the profile projection data to identify features representing spots in the bounded area.

Still further, the step of processing includes the step of calculating a best fitted pitch value using an outlier removal based line fitting algorithm.

The step of processing also includes the step of calculating distance between adjacent rows of arrays and distance between adjacent columns of arrays.

Further, in carrying out the above objects and other objects of the present invention, a system for carrying out the above method steps and a computer-readable storage medium having a program for executing the method are provided.

The above objects and other objects, features, and advantages of the present invention are readily apparent from the following detailed description of the best mode for carrying out the invention when taken in connection with the accompanying drawings.

BEST MODE FOR CARRYING OUT THE INVENTION

Figure 5:
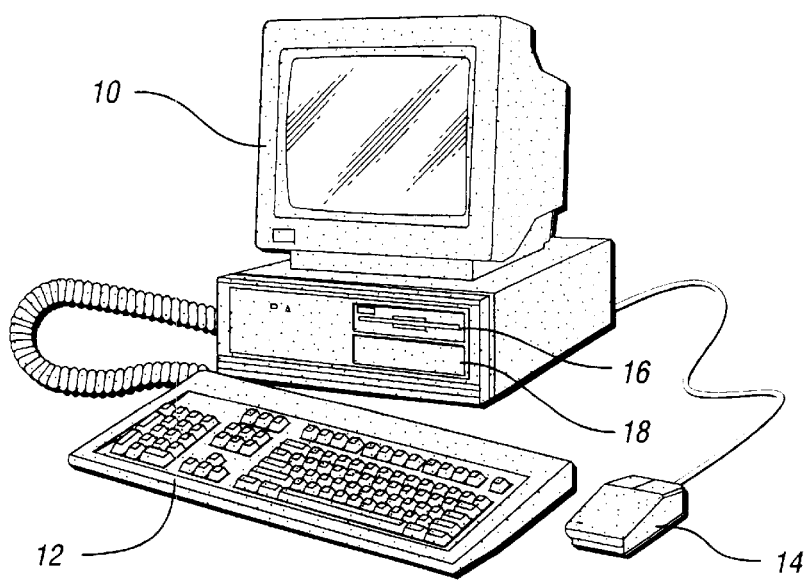
FIG. 5 is a schematic diagram illustrating a preferred hardware configuration on which the method of the present invention can be implemented.

Referring now to the drawing figures, there is illustrated in FIG. 5 a workstation on which the method and system of the present invention can be implemented. However, other configurations are possible. The hardware illustrated in FIG. 5 includes a monitor 10 such as a single SVGA display, a keyboard 12, a pointing device such as a mouse 14, a magnetic storage device 16, and a chassis 18 including a CPU and random access memory. The monitor 10 may be a touch screen monitor used in addition to standard keyboard/ mouse interaction. In a preferred embodiment, the chassis 18 is a Pentium-based IBM compatible PC or other PC having at least 32 megabytes of RAM and at least 12 megabytes of hard disk space. The workstation typically includes a Windows NT, graphical user interface as well as an Ethernet 10 Base-T high speed Lan network interface.

Figure 1:
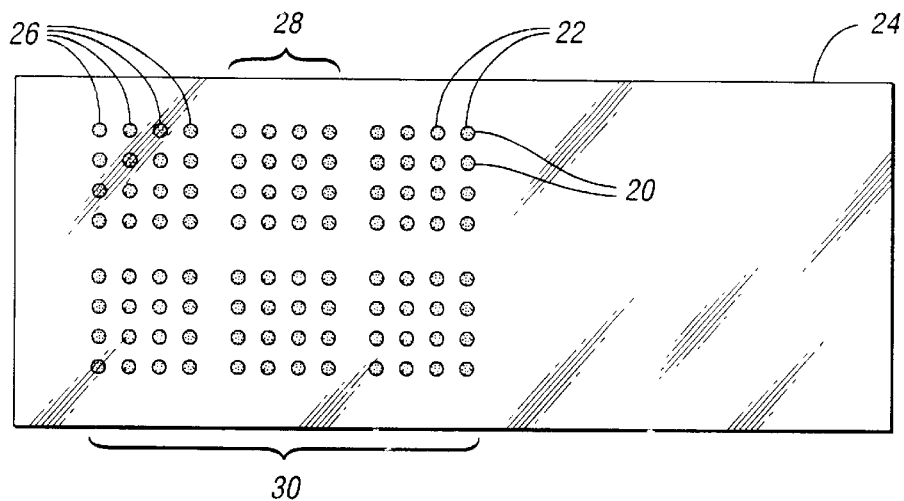
FIG. 1 is a top plan schematic view illustrating a spot, an array and an array set on a glass slide.
Figure 2:
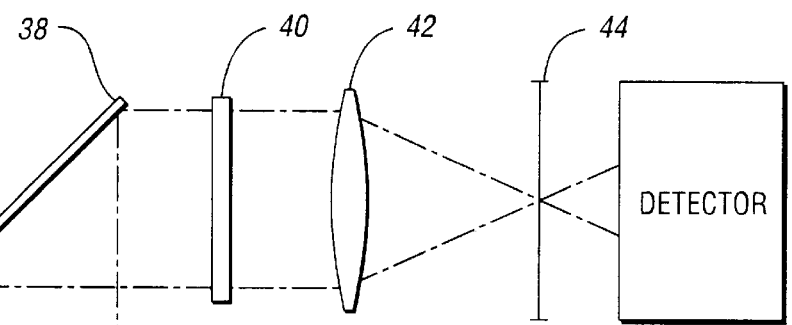
FIG. 2 is a schematic view of a confocal laser reader used to generate digital images.
Figure 3:
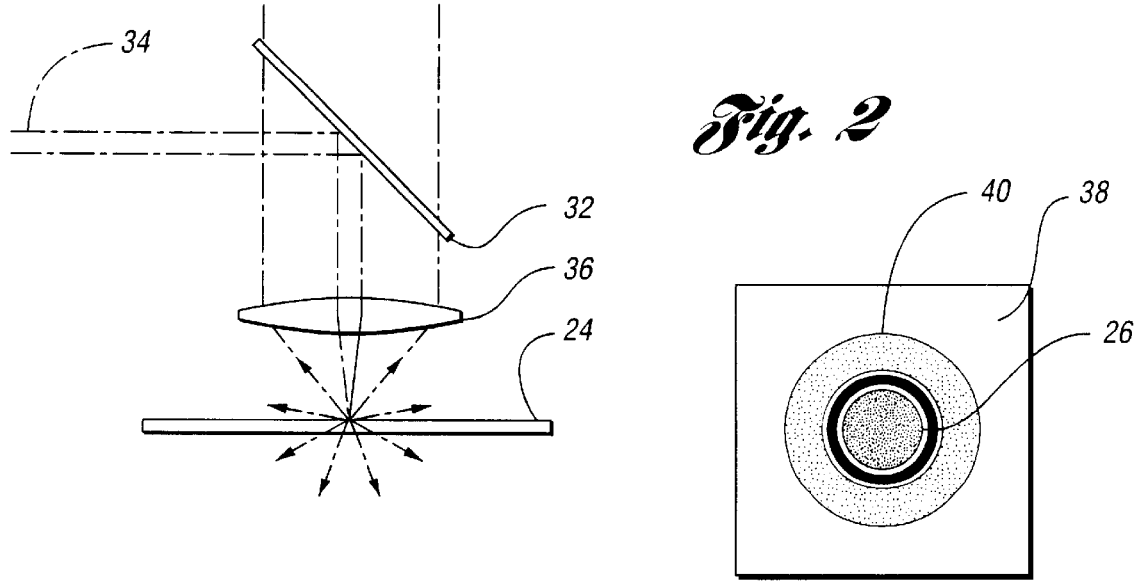
FIG. 3 is a schematic view of a spot used for local area calculations.
Figure 4:
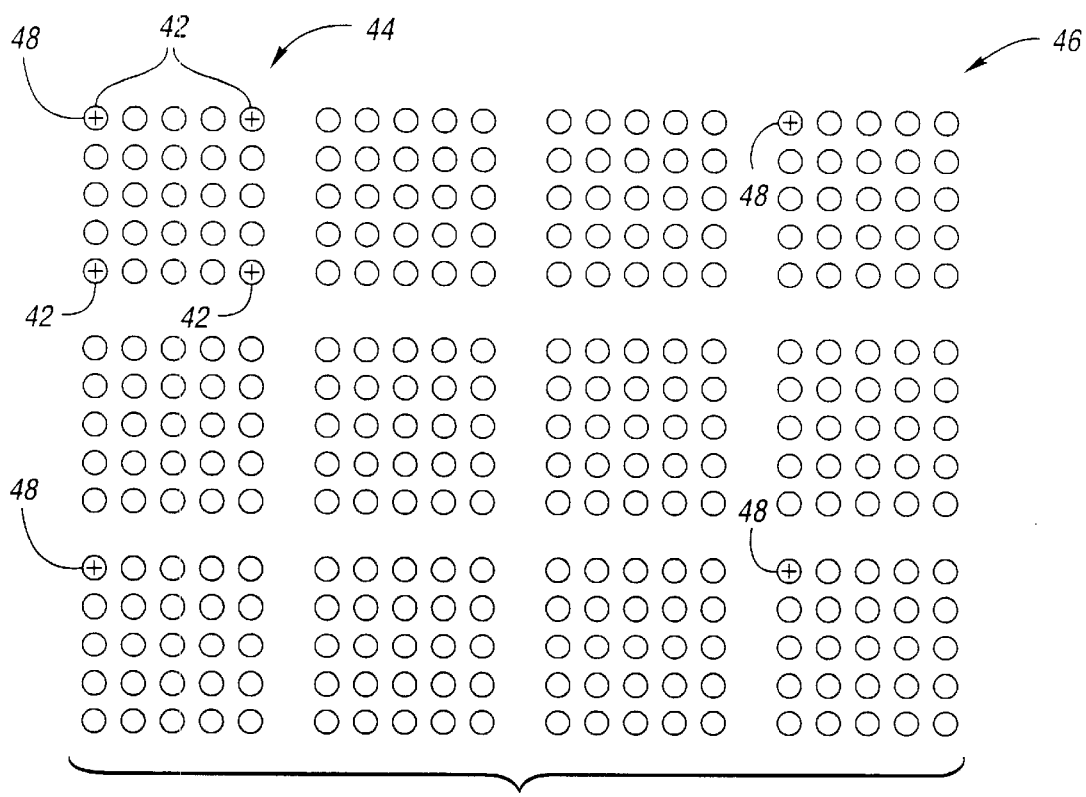
FIG. 4 is a schematic view of a prior art array of spots wherein manual selection is provided.
Figure 13:
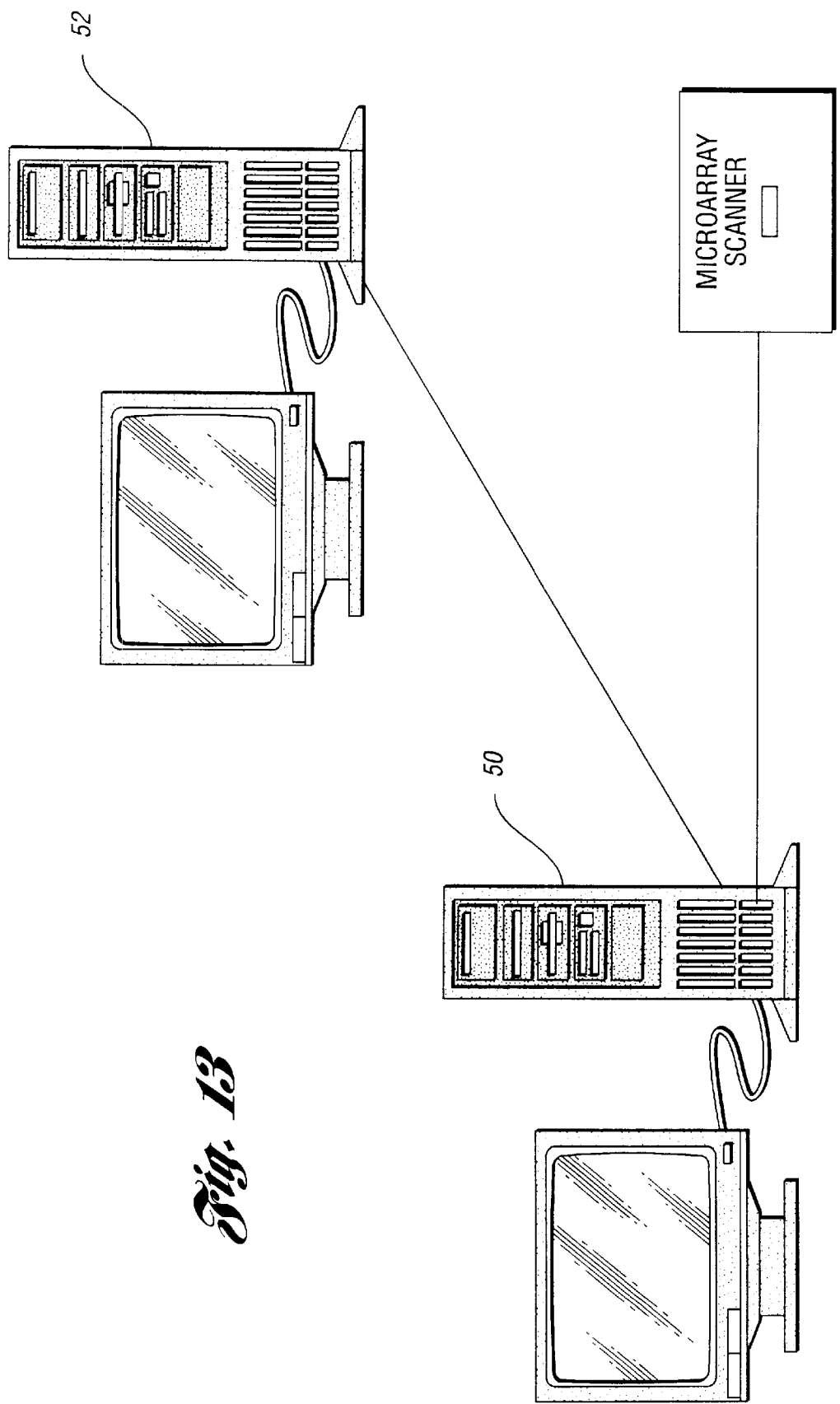
FIG. 13 is a schematic view of a system in which the present invention can be utilized.

One or more images are obtained by a user from the microarray reader or scanner of FIGS. 2 and 13. The scanner is controlled by a scanner control computer 50 which, in turn, is also networked to a quantitation computer 52. One or more of these images are used in the process of the invention to create the microarray pattern.

Figure 12:
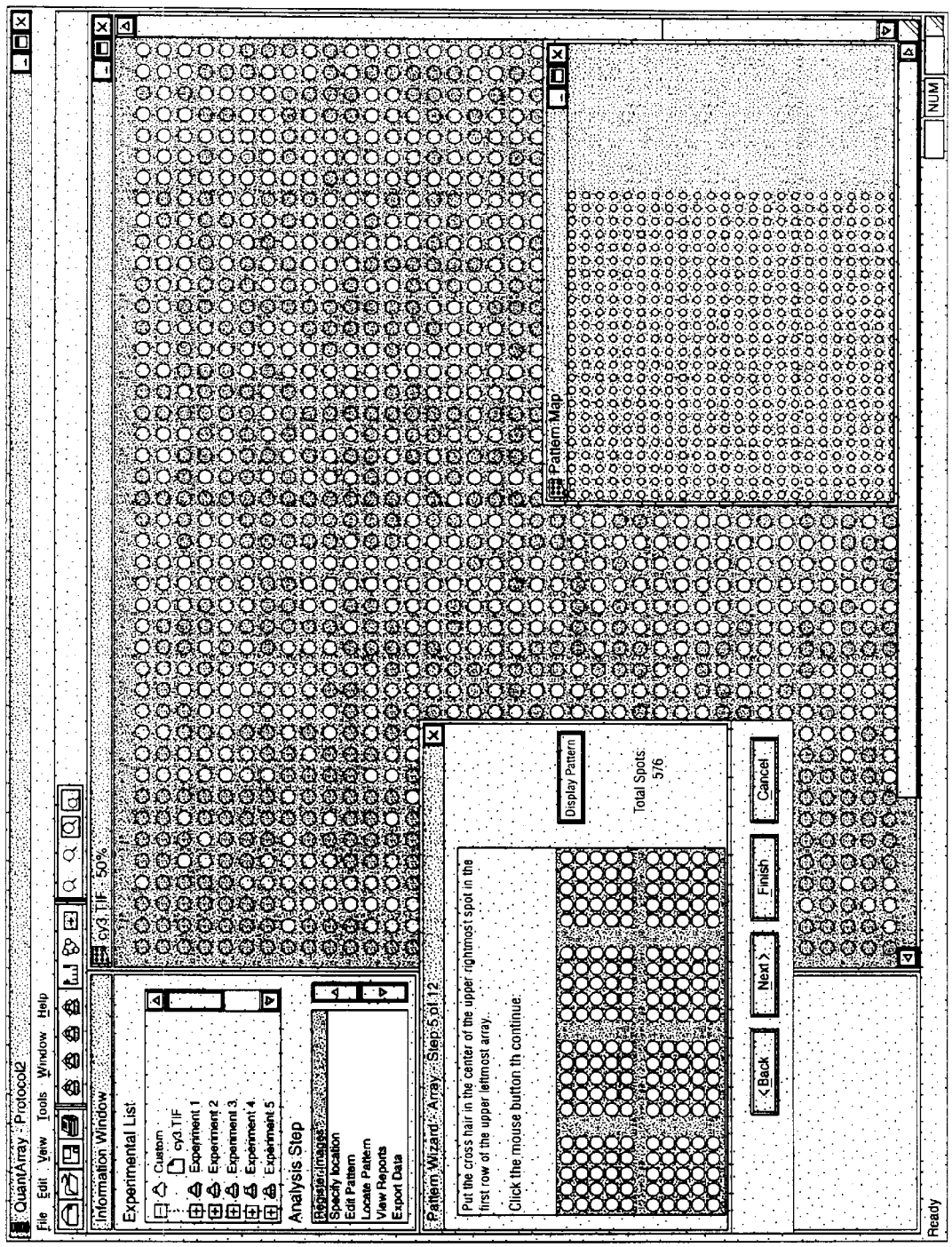
FIG. 12 is a schematic view of a pattern generator of the present invention.

Listed below are seven steps typically used in the creation of a microarray pattern. This invention also envisions ways of automatically creating the grid pattern with either fewer or more steps. During each of these seven steps, the user is directed by the software to point and click on different areas of any of the images displayed in FIG. 12 on the monitor 10 with the use of a pointing device such as the mouse 14. The software internally records each of the positions for later use in calculating the key parameters of the grid pattern. Fewer steps in the process can be envisioned by removing the fourth and sixth steps which may require more sophisticated software algorithms to calculate the correct number of rows and columns and the respective spacing between each.

Figure 6:
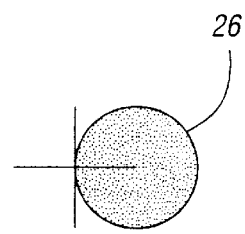
FIG. 6 is a schematic view of a spot with spot edge selection for use in calculating spot diameter.

Step 1: Point and click on the left edge of any spot 26 as illustrated in FIG. 6.

Step 2: Point and click on the right edge of the same spot used in step 1. These two values are used to calculate the typical spot diameter within the array pattern to be quantitated.

Figure 7:
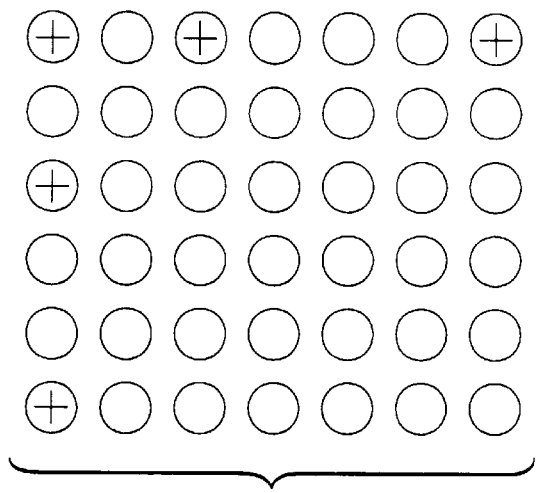
FIG. 7 is a schematic view of an array of spots illustrating center selections of the method of the present invention.

Step 3: Point and click on the center of the spot in the upper left corner of the array of FIG. 7. This data provides the origin of the entire array pattern and the basis for calculating the spacing and number of spots in each row and column.

Step 4: (optional) Point and click on the third spot in the first row of FIG. 7. This provides an estimate of the spacing between columns of spots for use in the final more accurate, calculation of the column spacing. The algorithm is not restricted to the third spot in the row and can reasonably use any spot after the first and before the last spot in the row.

Step 5: Point and click on the last spot on the first row of FIG. 7. This provides the software of the invention with all the information it needs to calculate the number of spots in each row and the average distance between each spot.

Figure 8:
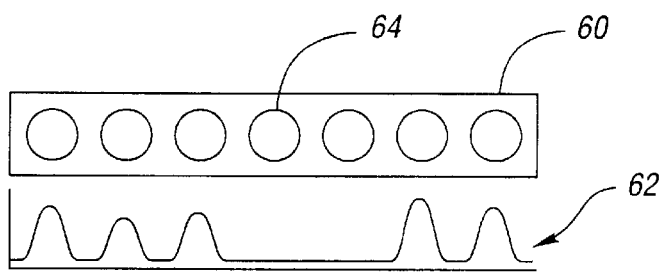
FIG. 8 is a schematic view illustrating a row area and a corresponding profile projection.

As illustrated in FIG. 8, the image processing algorithm creates a bounded area 60 which encompasses the first row of spots, using the diameter from steps 1 and 2 and the estimated spacing distance from step 3. It performs a profile projection 62 of the image data found in this defined area 60, wherein the least expressed spot is designated at 64. The software then calculates a spot model projection from the spot diameter and uses it as a correlation model to compare against sections corresponding to each spot along the full spot row's profile projection. The correlation model will minimize the chances of noise or other image artifacts from being considered in the spacing calculations. The software of the invention then calculates a correlation coefficient between the model and each similar feature within the profile projection data with each match being tagged for later use.

Figure 9:
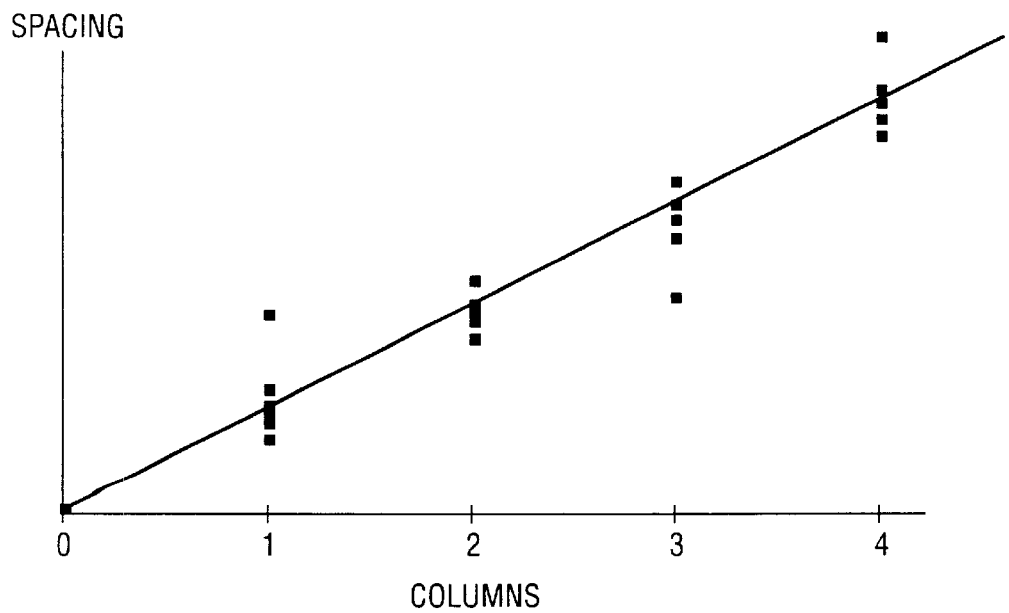
FIG. 9 is a graph of distance versus number of columns between each spot.

The software then uses the estimated spacing calculated from steps 3 and 4 to create a plot of the X distance versus the number of columns between each feature identified by the previous correlation step. See FIG. 9. Once all features representing spots have been added to the graph, the outliers are removed and a regression line is fit to the remaining data points, yielding a line equation in the slope-intercept form y=mx+b. The column spacing is the slope, m, of the calculated line.

Once the calculation is complete the software of the invention may display the value on the monitor 10 for visual feedback to the user.

Step 6: (optional) Point and click on the first spot in the third row. This provides an estimate of the spacing between rows of spots for use in the final, more accurate calculation of the row spacing. The algorithm is not restricted to the first spot in the third row and can reasonably use the first spot in any row after the first and before the last.

Step 7: Point and click on the first spot in the last row. This provides the software of the invention with all the information it needs to calculate the number of spots in each column and the average distance between each spot. The software then performs the image processing algorithm described in step 5 for the final calculations.

Figure 10:
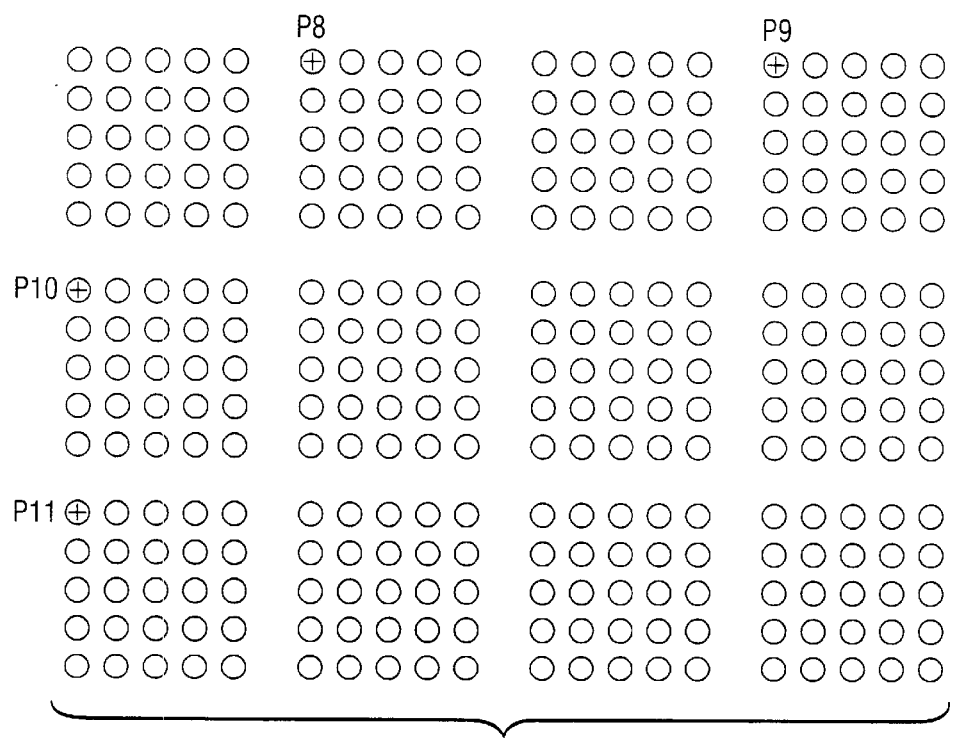
FIG. 10 is a schematic view of an array of spots illustrating array set selections.

The invention is extended to cover the calculation of the number of rows and columns of an array set and the distances between each row and column by adding an additional four steps. See FIG. 10. These additional steps will allow the software of the invention to automatically calculate the number of arrays in each row and column.

Step 8: Point and click on the first spot P8 in the first row of the array just to the right of the array used in steps 1 through 7.

Figure 11:
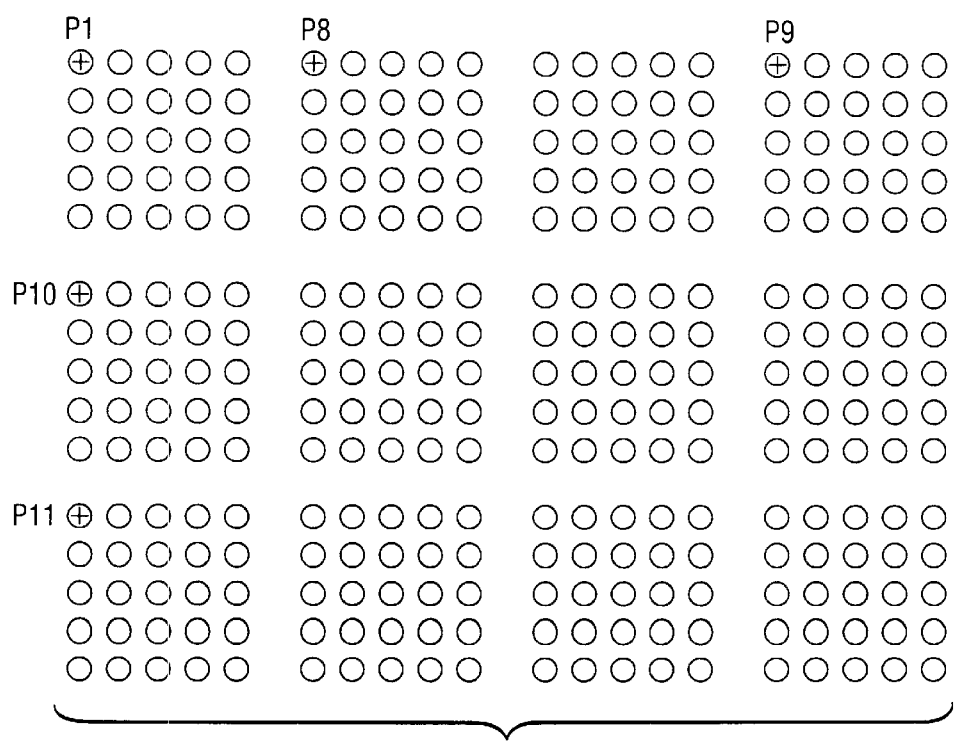
FIG. 11 is a schematic view of an array of spots illustrating array spacing and number of array calculations.

Step 9: Point and click on the first spot P9 in the first row of the last array to the right of the array used in steps 1 through 7. The distance between the points in step 1 and step 8 is used to calculate the number of arrays along the first row of the microarray and the average distance between arrays. The formulas for these calculations are as follows (see FIG. 11):

$$\text{Number of arrays,} \quad N_1 = |P9 - P1|/|P8 - P1| + 1$$

$$\text{Array spacing distance,} \quad D_1 = |P9 - P1|/(N_1 - 1) \text{ if } N_1 \neq 0$$

$$|P9 - P1| \text{ if } N_1 = 0$$

The algorithm described in step 5 to calculate the number of objects and average spacing can easily be adapted to calculate the number of arrays and the spacing between them.

Step 10: Point and click on the first spot P10 on the first row of the second array just below the array used in steps 1 through 7.

Step 11: Point and click on the first spot P11 in the first row of the last array below the array used in steps 1 through 7. The distance between the points in step 1 and step 10 is used to calculate the number of arrays along the first column of the microarray and the average distance between arrays. The formulas for these calculations are as follows (see FIG. 11):

$$\text{Number of arrays,} \quad N_2 = |P11 - P1|/|P10 - P1| + 1$$

$$\text{Array spacing distance,} \quad D_2 = |P11 - P1|/(N_2 - 1) \text{ if } N_1 \neq 1$$

$$|P11 - P1| \text{ if } N_2 = 1$$

The algorithm described in step 5 to calculate the number of objects and average spacing can easily be adapted to calculate the number of arrays and the spacing between them.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for interactively developing a regular pattern of grid patterns including at least one grid pattern from at least one digital image of rows and columns of spots, the regular pattern of grid patterns defining an array set, and the rows and columns of spots defining rows and columns of arrays, the method comprising:

displaying the rows and columns of spots including a corner spot located in one of the rows and columns;

receiving a first set of commands from a user to select an approximate location of the corner spot to obtain pattern origin data;

receiving a second set of commands from the user to select at least one column spot in the same column as the corner spot to obtain column data wherein the at least one column spot includes a spot furthest away from the corner spot, and wherein the column data is processed with the pattern origin data and the at least one digital image to obtain the at least one grid pattern;

receiving a third set of commands from the user to select at least one row corner spot in the row of arrays corresponding to the corner spot of the at least one grid pattern to obtain row array data wherein the at least one row corner spot is in an array furthest from the at least one grid pattern in the same row of arrays as the at least one grid pattern; and receiving a fourth set of commands from the user to select at least one column corner spot in the column of arrays corresponding to the corner spot of the at least one grid pattern to obtain column array data wherein the at least one column corner spot is in an array furthest from the at least one grid pattern in the same column of arrays; and processing the at least one digital image and the pattern origin data to obtain the at least one grid pattern, wherein the at least one grid pattern includes rows and columns of grid elements, wherein the step of processing includes the step of calculating the number of rows and columns of grid elements, average spacing between adjacent rows and average spacing between adjacent columns of grid elements, and wherein processing also processes the row array data and the column array data with the spot dimension data, the pattern origin data and the row and column data to obtain the regular pattern of grid patterns.

2. The method as claimed in claim 1 further comprising receiving a fifth set of commands from the user to select at least one edge of one of the spots to obtain spot dimension data, wherein the spot dimension data is processed with the pattern origin data and the at least one digital image to obtain the at least one grid pattern.

3. The method as claimed in claim 2 wherein the step of receiving the fifth set of commands from the user selects two opposite edges of the one of the spots and wherein the spot dimension data is spot diameter data.

4. The method as claimed in claim 2 wherein the step of processing includes the step of processing the spot dimension data and the pattern origin data to obtain a bounded area of image data which encompasses either the row or the column of spots including the corner spot.

5. The method as claimed in claim 4 wherein the step of processing includes the step of performing a profile projection of the image data in the bounded area to obtain profile projection data.

6. The method as claimed in claim 5 wherein the step of processing includes the step of calculating a spot model projection based on the spot dimension data.

7. The method as claimed in claim 6 wherein the step of processing includes the steps of utilizing the spot model projection as a correlation model and comparing the correlation model with sections corresponding to each spot along the profile projection in the bounded area.

8. The method as claimed in claim 7 wherein the step of processing includes the step of calculating a correlation coefficient between the correlation model and each similar feature within the profile projection data to identify features representing spots in the bounded area.

9. The method as claimed in claim 8 wherein the step of processing includes the step of calculating a best fitted pitch value using an outlier removal based line fitting algorithm.

10. The method as claimed in claim 1 further comprising receiving a sixth set of commands from the user to select at least one row spot in the same row as the corner spot to obtain row data wherein the at least one row spot includes a spot furthest away from the corner spot, and wherein the row data is processed with the pattern origin data and the at least one digital image to obtain the at least one grid pattern.

11. The method as claimed in claim 10 wherein the step of receiving the sixth set of commands selects two row spots in the same row as the corner spot to obtain the row data.

12. The method as claimed in claim 1 wherein the step of receiving the second set of commands selects two column spots in the same column as the corner spot to obtain the column data.

13. The method as claimed in claim 1 wherein the at least one grid pattern is a microarray pattern.

14. The method as claimed in claim 1 wherein each of the grid patterns is a microarray pattern.

15. The method as claimed in claim 1 wherein the step of receiving the third set of commands selects two row corner spots in the same row of arrays as the at least one grid pattern to obtain the row array data.

16. The method as claimed in claim 1 wherein the step of receiving the fourth set of commands selects two column corner spots in the same column of arrays as the at least one grid pattern to obtain the column array data.

17. The method as claimed in claim 1 further comprising displaying a value representing distance between columns or rows of spots.

18. The method as claimed in claim 1 wherein the step of processing includes the step of calculating distance between adjacent rows of arrays and distance between adjacent columns of arrays.

19. A system for interactively developing a regular pattern of grid patterns including at least one grid pattern from at least one digital image of rows and columns of spots, the regular pattern of grid patterns defining an array set, and wherein the rows and columns of spots define rows and columns of arrays, the system comprising:

means for displaying the rows and columns of spots including a corner spot located in one of the rows and columns;

means for:

receiving a first set of commands from a user to select an approximate location of the corner spot to obtain pattern origin data;

receiving a second set of commands from a user to select at least one column spot in the same column as the corner spot to obtain column data wherein the at least one column spot includes a spot furthest away from the corner spot, wherein the column data is processed with the pattern origin data and the at least one digital image to obtain the at least one grid pattern;

receiving a third set of commands from the user to select at least one row corner spot in the row of arrays corresponding to the corner spot of the at least one grid pattern to obtain row array data wherein the at least one row corner spot is in an array furthest from the at least one grid pattern in the same row of arrays as the at least one grid pattern; and receiving a fourth set of commands from the user to select at least one column corner spot in the column of arrays corresponding to the corner spot of the at least one grid pattern to obtain column array data wherein the at least one column corner spot is in an array furthest from the at least one grid pattern in the same column of arrays; and means for processing the pattern origin data and the at least one digital image to obtain the at least one grid pattern, wherein the at least one grid pattern includes rows and columns of grid elements, the means for processing includes means for calculating the number of rows and columns of grid elements, average spacing between adjacent rows and average spacing between adjacent columns, and wherein the means for processing also processes the row array data and the column array data with the spot dimension data, the pattern origin data and the row and column data to obtain the regular pattern of grid patterns.

20. The system as claimed in claim 19 further comprising means for receiving a fifth set of commands from the user to select at least one edge of one of the spots to obtain spot dimension data, wherein the spot dimension data is processed with the pattern origin data and the at least one digital image to obtain the at least one grid pattern.

21. The system as claimed in claim 20 wherein the fifth set of commands from the user selects two opposite edges of the one of the spots and wherein the spot dimension data is spot diameter data.

22. The system as claimed in claim 20 wherein the means for processing processes the spot dimension data and the pattern origin data to obtain a bounded area of image data which encompasses either the row or the column of spots including the corner spot.

23. The system as claimed in claim 22 wherein the means for processing includes means for performing a profile projection of the image data in the bounded area to obtain profile projection data.

24. The system as claimed in claim 23 wherein the means for processing includes means for calculating a spot model projection based on the spot dimension data.

25. The system as claimed in claim 24 wherein the means for processing utilizes the spot model projection as a correlation model and compares the correlation model with sections corresponding to each spot along the profile projection in the bounded area.

26. The system as claimed in claim 25 wherein the means for processing includes means for calculating a correlation coefficient between the correlation model and each similar feature within the profile projection data to identify features representing spots in the bounded area.

27. The system as claimed in claim 26 wherein the step for processing includes means for calculating a best fitted pitch value using an outlier removal based line fitting algorithm.

28. The system as claimed in claim 19 further comprising means for receiving a sixth set of commands from the user to select at least one row spot in the same row as the corner spot to obtain row data wherein the at least one row spot includes a spot furthest away from the corner spot, wherein the row data is processed with the pattern origin data and the at least one digital image to obtain the at least one grid pattern.

29. The system as claimed in claim 28 wherein the sixth set of commands selects two row spots in the same row as the corner spot to obtain the row data.

30. The system as claimed in claim 28 wherein the means for processing includes the means for calculating distance between adjacent rows of arrays and distance between adjacent columns of arrays.

31. The system as claimed in claim 19 wherein the second set of commands selects two column spots in the same column as the corner spot to obtain the column data.

32. The system as claimed in claim 19 wherein the at least one grid pattern is a microarray pattern.

33. The system as claimed in claim 19 wherein each of the grid patterns is a microarray pattern.

34. The system as claimed in claim 19 wherein the third set of commands selects two row corner spots in the same one of arrays as the at least one grid pattern to obtain the row array data.

35. The system as claimed in claim 19 wherein the fourth set of commands selects two column corner spots in the same column of arrays as the at least one grid pattern to obtain the column array data.

36. The system as claimed in claim 19 further comprising means for displaying a value representing distance between columns or rows of spots.

37. A computer-readable storage medium having stored therein a program which interactively develops a regular pattern of grid patterns including at least one grid pattern from at least one digital image of rows and columns of spots, the regular pattern of grid patterns defining an array set, and the rows and columns of spots defining rows and columns of arrays by executing the steps of:

displaying the rows and columns of spots including a corner spot located in one of the rows and columns;

receiving a first set of commands from a user to select an approximate location of the corner spot to obtain pattern origin data;

receiving a second set of commands from the user to select at least one column spot in the same column as the corner spot to obtain column data wherein the at least one column spot includes a spot furthest away from the corner spot, and wherein the column data is processed with the pattern origin data and the at least one digital image to obtain the at least one grid pattern;

receiving a third set of commands from the user to select at least one row corner spot in the row of arrays corresponding to the corner spot of the at least one grid pattern to obtain row array data wherein the at least one row corner spot is in an array furthest from the at least one grid pattern in the same row of arrays as the at least one grid pattern;

receiving a fourth set of commands from the user to select at least one column corner spot in the column of arrays corresponding to the corner spot of the at least one grid pattern to obtain column array data wherein the at least one column corner spot is in an array furthest from the at least one grid pattern in the same column of arrays; and processing the pattern origin data and the at least one digital image to obtain the at least one grid pattern, wherein the at least one grid pattern includes rows and columns of grid elements, wherein the step of processing includes the step of calculating the number of rows and columns of grid elements, average spacing between adjacent rows and average spacing between adjacent columns of grid elements, and wherein processing also processes the row array data and the column array data with the spot dimension data, the pattern origin data and the row and column data to obtain the regular pattern of grid patterns.

38. The storage medium as claimed in claim 37 wherein the program further executes the step of receiving a fifth set of commands from the user to select at least one edge of one of the spots to obtain spot dimension data, and wherein the spot dimension data is processed with the pattern origin data and the at least one digital image to obtain the at least one grid pattern.

39. The storage medium as claimed in claim 38 wherein the step of receiving the fifth set of commands from the user selects two opposite edges of the one of the spots and wherein the spot dimension data is spot diameter data.

40. The storage medium as claimed in claim 38 wherein the step of processing includes the step of processing the spot dimension data and the pattern origin data to obtain a bounded area of image data which encompasses either the row or the column of spots including the corner spot.

41. The storage medium as claimed in claim 40 wherein the step of processing includes the step of performing a profile projection of the image data in the bounded area to obtain profile projection data.

42. The storage medium as claimed in claim 41 wherein the step of processing includes the step of calculating a spot model projection based on the spot dimension data.

43. The storage medium as claimed in claim 42 wherein the step of processing includes the steps of utilizing the spot model projection as a correlation model and comparing the correlation model with sections corresponding to each spot along the profile projection in the bounded area.

44. The storage medium as claimed in claim 43 wherein the step of processing includes the step of calculating a correlation coefficient between the correlation model and each similar feature within the profile projection data to identify features representing spots in the bounded area.

45. The storage medium as claimed in claim 44 wherein the step of processing includes the step of calculating a best fitted pitch value using an outlier removal based line fitting algorithm.

46. The storage medium as claimed in claim 37 wherein the program further executes the step of receiving a sixth set of commands from the user to select at least one row spot in the same row as the corner spot to obtain row data wherein the at least one row spot includes a spot furthest away from the corner spot, and wherein the row data is processed with the pattern origin data and the at least one digital image to obtain the at least one grid pattern.

47. The storage medium as claimed in claim 46 wherein the step of receiving the sixth set of commands selects two row spots in the same row as the corner spot to obtain the row data.

48. The storage medium as claimed in claim 37 wherein the step of receiving the second set of commands selects two column spots in the same column as the corner spot to obtain the column data.

49. The storage medium as claimed in claim 41 wherein the at least one grid pattern is a microarray pattern.

50. The storage medium as claimed in claim 37 wherein each of the grid patterns is a microarray pattern.

51. The storage medium as claimed in claim 37 wherein the step of receiving the third set of commands selects two row corner spots in the same one of arrays as the at least one grid pattern to obtain the row array data.

52. The storage medium as claimed in claim 37 wherein the step of receiving the fourth set of commands selects two column corner spots in the same column of arrays as the at least one grid pattern to obtain the column array data.

53. The storage medium as claimed in claim 37 wherein the program further executes the step of displaying a value representing distance between columns or rows of spots.

54. The storage medium as claimed in claim 37 wherein the step of processing includes the step of calculating distance between adjacent rows of arrays and distance between adjacent columns of arrays.

* * * * *